United States Patent [19]

Gray

[11] Patent Number: 5,318,042

[45] Date of Patent: Jun. 7, 1994

[54] CONDOM

[75] Inventor: Ian M. B. Gray, Cape Town, South Africa

[73] Assignee: Oxacon Limited, Tortola, British Virgin Isls.

[21] Appl. No.: 849,028

[22] PCT Filed: Oct. 23, 1990

[86] PCT No.: PCT/GB90/01626

§ 371 Date: Apr. 22, 1992

§ 102(e) Date: Apr. 22, 1992

[87] PCT Pub. No.: WO91/06268

PCT Pub. Date: May 16, 1991

[30] Foreign Application Priority Data

Oct. 24, 1989 [ZA] South Africa ............... 89/8054

[51] Int. Cl.$^5$ .................................... A61F 6/04
[52] U.S. Cl. .................. 128/844; 128/918; 604/349
[58] Field of Search ............ 128/842, 844, 918; 604/347-352

[56] References Cited

U.S. PATENT DOCUMENTS

| D. 253,009 | 9/1979 | Okamoto ............ 128/844 X |
| D. 254,808 | 4/1980 | Meldahl . |
| 2,358,440 | 9/1944 | Bowman ............ 128/844 X |
| 3,759,254 | 9/1973 | Clark . |
| 4,232,675 | 11/1980 | Meldahl . |
| 4,354,494 | 10/1982 | Hogin . |

FOREIGN PATENT DOCUMENTS

| 1935574 | 1/1971 | Fed. Rep. of Germany . |
| 8811772 | 12/1988 | Fed. Rep. of Germany . |
| 1250553 | 10/1971 | United Kingdom ............ 128/844 |
| 1252255 | 11/1971 | United Kingdom ............ 128/844 |
| 2100988 | 1/1983 | United Kingdom ............ 128/844 |

*Primary Examiner*—Randall L. Green
*Assistant Examiner*—Mary Beth Jones
*Attorney, Agent, or Firm*—Curtis, Morris & Safford

[57] ABSTRACT

A condom which has a sheath which is open at one end and closed at the other. The sheath includes a cylindrical portion of constant diameter and a portion of larger diameter between the portion of constant diameter and the open end. The open end is encircled by a ring which is of the same diameter as the constant diameter portion. The two portions are co-axial. The portion of larger diameter in use provides a pouch intended to receive and envelope the wearer's scrotum and a region which is diametrically opposed to said pouch and which ruffles thereby providing a series of circumferentially extending ridges which ridges inhibit blood flow from the penis and provide for female stimulation. In a modified form there is a teat at the closed end. In another form there is a further portion of constant diameter, smaller than the larger diameter portion, between said latter portion and the open end.

7 Claims, 1 Drawing Sheet

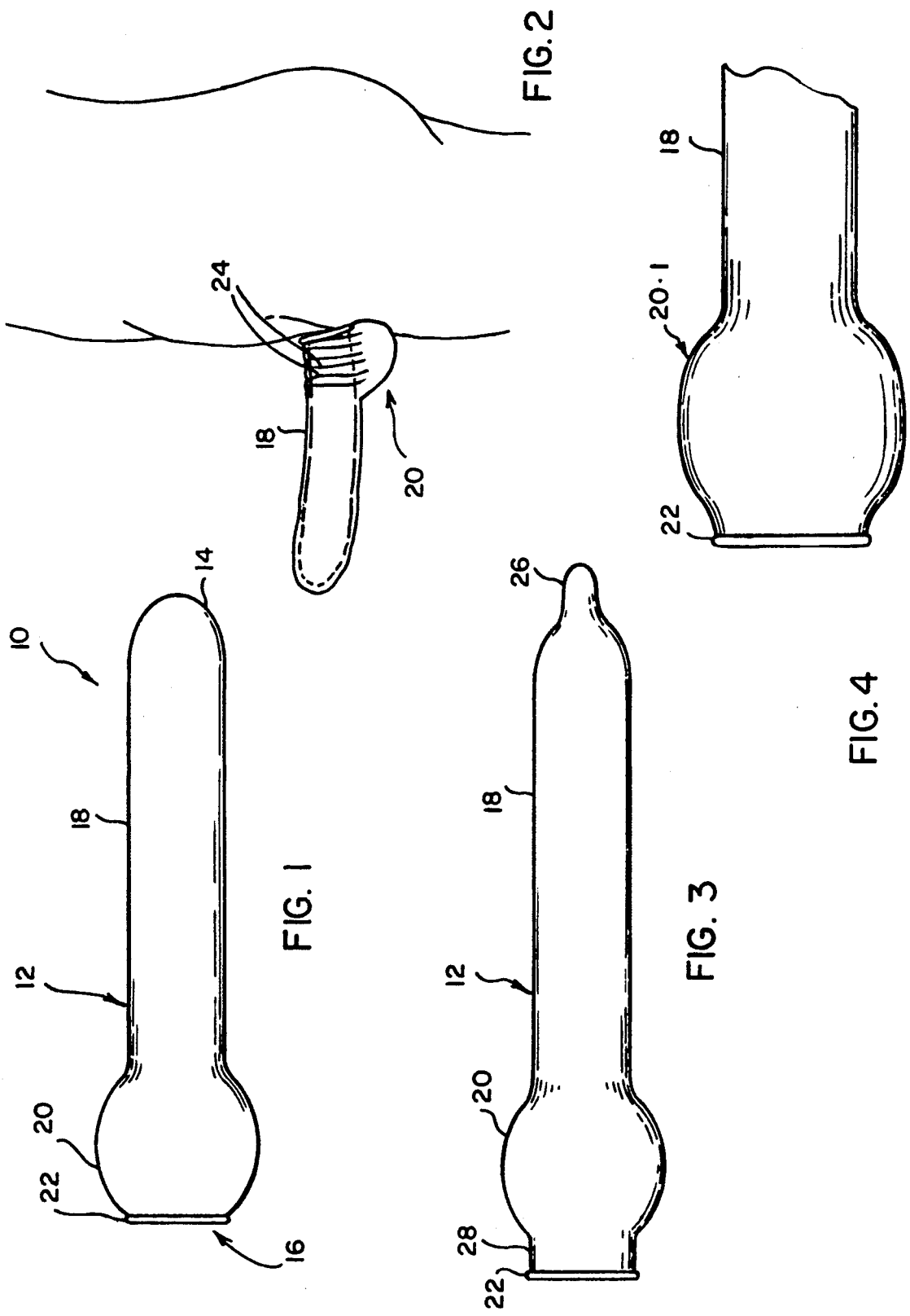

CONDOM

This invention relates to a condom.

The condom which is sold in the largest numbers comprises a sheath which is closed at one end and open at the other, the sheath being of constant diameter throughout its length. The closed end may be extended by a short, smaller diameter teat. Condoms have been proposed which include a "downward" extension at said open end, the extension forming a bag for receiving the user's scrotum. These extended types are not, to the best of applicant's knowledge, available commercially, or are not widely available commercially. The main reasons for this are that they are difficult to make, package, apply and use. They are also subjected to stresses in use which can cause splitting and consequent failure.

The present invention seeks to provide a condom which envelops the scrotum, which is easy to manufacture, package, apply and use and does not have the potential failure problem set out above.

According to the present invention there is provided a condom comprising a sheath which is closed at one end and open at the other end, said sheath including a cylindrical portion the diameter of which is constant, said portion extending from the closed end of the sheath towards the open end and there being an elastic ring encircling said open end, characterised in that there is a portion of larger diameter than said cylindrical portion of constant diameter between the latter portion and said open end, the diameter of the elastic ring being less than the diameter of the larger diameter portion, the larger diameter portion being co-axial with said portion of constant diameter and with the ring and in use providing a pouch intended to receive and envelope the wearer's scrotum and a region which is diametrically opposed to said pouch and which ruffles thereby providing a series of circumferentially extending ridges adjacent the pubic bone, which ridges inhibit blood flow from the penis and provide for female stimulation.

In the preferred form said larger diameter portion is contiguous with said ring. However, it is possible to provide a further portion of constant diameter between said ring and said larger diameter portion, said further portion being smaller than said larger diameter portion. Said portion of constant diameter and said further portion can be of the same diameter.

In one form said portion of larger diameter has the form of a generally hemispherical bulb which merges on one side with said portion of constant diameter and narrows down to said ring on the other side. In another form said portion of larger diameter has a central part which is generally cylindrical, a first end part which merges smoothly with said portion of constant diameter and a second end part which decreases in diameter down to the diameter of the ring.

Said cylindrical portion of constant diameter can, at said closed end, be extended by a teat.

For a better understanding of the present invention, and to show how the same may be carried into effect, reference will now be made, by way of example, to the accompanying drawing in which:

FIG. 1 is a side elevation of a first form of condom in accordance with the present invention;

FIG. 2 is a diagrammatic side view showing the condom in use;

FIG. 3 is an elevation showing certain modifications to the condom; and

FIG. 4 illustrates a further modified form.

Referring firstly to FIG. 1, the condom illustrated is generally designated 10 and comprises a sheath 12 which is closed at one end, the right-hand end, by a generally hemispherical wall 14 and open at the other end. The open end is designated 16. The condom is manufactured using any of the materials which are presently employed in the manufacture of condoms.

The sheath 12 includes a portion 18 which is of constant diameter, the portion 18 extending away from the hemispherical closed end 14 towards the open end 16. Between the portion 18 and the open end 16 is a portion 20 of larger diameter. The portion 20, like the portion 18, is circular in cross section and the two portions are co-axial with one another. In the form illustrated in FIG. 1 the portion 20 forms a "bulb" being generally hemispherical in shape. The portion 20 is contiguous with the open end 16, there being a retaining ring 22 immediately adjacent the portion 20 and encircling the open end 16.

Simply by way of example, the portion 18 can be 205 mm in length and have a transverse dimension of 50 mm when flattened. The portion 20 can have an axial dimension of approximately 75 mm and a transverse dimension, when flattened, of 75 mm. This means that when "inflated" to cylindrical form but not stretched the diameter of the portion 18 is 32 mm and the diameter of the portion 20 is 48 mm.

Referring now to FIG. 2, it will be seen that the major part of the length of the user's penis is received in the portion 18. The portion 20 forms a pouch which receives the part of the penis adjacent the pubic bone and also receives the scrotum. Because the portions 18 and 20 are concentric, the portion 20 must be pulled downwardly and backwards during fitting and this causes the diametrically opposed upper part of the portion 20 to ruffle, as illustrated in FIG. 2, thereby to form a series of ridges 24. The ridges 24 are generally parallel with one another and extend through somewhat over 180° of the circumferential extent of the portion 20. The ridges are of greatest height where they cross the top surface of the penis and decrease in height finally running out as illustrated in FIG. 2. The ridges 24, and the ring 22 which fits in the natural groove adjacent the pubic bone, tend to restrict blood flow out of the penis through the blood flow passages which are along the top of the penis. There are no ridges 24 below the penis and the ring 22 does not exert sufficient constricting action to restrict blood flow into the penis. This enhances the erection and also provides for female stimulation.

In the modification of FIG. 3, there is a teat 26 which forms an extension of the portion 18 at the closed end and a cylindrical portion 28 between the ring 22 and the portion 20. The portion 28 can be of larger diameter than the portion 18 or of smaller diameter than the portion 18, but is preferably of the same diameter as the portion 18. It will be understood that a teat 26 can be incorporated into the condom of FIG. 1.

Turning finally to FIG. 4, this shows a condom in which the portion of greater diameter, designated 20.1, is elongated with respect to the portion 20 of FIG. 1 thereby to provide a generally cylindrical centre part and an end part which merges smoothly with the portion 18. The overall length of the condom of FIG. 4 may be increased somewhat with respect to the length of the condom of FIG. 1.

I claim:

1. A condom having an open end, a closed end and an elastic ring encircling said open end, the condom having a length, a first portion constituting a major part of the length of the condom and a second portion constituting a minor part of the length of the condom, said portions and said ring being co-axial with the one another and the second portion being between said first portion and said open end, said first portion being of cylindrical form and of smaller diameter than said second portion and the diameter of the elastic ring being less than the diameter of said second portion, said second portion in use providing a pouch adapted to receive and envelope the wearer's scrotum and also providing a region which is diametrically opposed to said pouch and which ruffles thereby adapted to provide a series of circumferentially extending ridges adjacent the pubic bone, which ridges inhibit blood flow from the penis and provide for female stimulation.

2. A condom according to claim 1, in which the second portion is contiguous with said ring.

3. A condom according to claim 1, in which there is a further cylindrical portion between said ring and said second portion, said further portion being smaller than said second portion.

4. A condom according to claim 3, in which said first portion is of constant diameter and said further portion is also of constant diameter and is of the same diameter as said first portion.

5. A condom according to claim 1, in which said second portion has the form of a generally hemispherical bulb which merges on one side with said first portion and narrows down to said ring on the other side.

6. A condom according to claim 1, in which said second portion has a central part which is generally cylindrical, a first end part which merges smoothly with said first portion and a second end part which decreases in diameter down to the diameter of the ring.

7. A condom according to claim 1, in which said first portion is, at said closed end, extended by a teat.

* * * * *

UNITED STATES PATENT AND TRADEMARK OFFICE
CERTIFICATE OF CORRECTION

PATENT NO. : 5,318,042
DATED : June 7, 1994
INVENTOR(S) : Ian Matthew Buchanan Gray It is certified that error appears in the above-identified patent and that said Letters Patent is hereby corrected as shown below:

Column 3:
  Claim 1, line 6, (column 3, line 6), delete "the".

Signed and Sealed this

Third Day of January, 1995

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,318,042
DATED : June 7, 1994
INVENTOR(S) : Ian Matthew Buchanan Gray It is certified that error appears in the above-indentified patent and that said Letters Patent is hereby corrected as shown below:

On the title page, item [73], change "Oxacon Limited" to --Ovacon Limited--.

Signed and Sealed this

Twenty-first Day of February, 1995

Attest:

BRUCE LEHMAN

Attesting Officer     Commissioner of Patents and Trademarks